(12) United States Patent
Liu et al.

(10) Patent No.: US 10,006,887 B2
(45) Date of Patent: *Jun. 26, 2018

(54) ADJUSTABLE FIXING DEVICE FOR ACOUSTIC EMISSION TEST SENSORS FOR ROCK DAMAGE TESTING

(71) Applicant: Sichuan University, Chengdu (CN)

(72) Inventors: Jianfeng Liu, Chengdu (CN); Yang Ju, Chengdu (CN); Jianliang Pei, Chengdu (CN); Lu Wang, Chengdu (CN); Huining Xu, Chengdu (CN); Yangmengdi Xu, Chengdu (CN); Feng Dai, Chengdu (CN); Wenxi Fu, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 215 days.

This patent is subject to a terminal disclaimer.

(21) Appl. No.: 15/016,326

(22) Filed: Feb. 5, 2016

(65) Prior Publication Data

US 2016/0231286 A1    Aug. 11, 2016

(30) Foreign Application Priority Data

Feb. 9, 2015   (CN) .......................... 2015 1 0066706

(51) Int. Cl.
  *G01N 29/14*   (2006.01)
  *G01N 29/04*   (2006.01)
  *G01N 29/22*   (2006.01)

(52) U.S. Cl.
  CPC .......... *G01N 29/14* (2013.01); *G01N 29/043* (2013.01); *G01N 29/223* (2013.01); *G01N 2291/0232* (2013.01)

(58) Field of Classification Search
  CPC ................. G01N 29/14; G01N 29/223; G01N 2291/0232

(Continued)

(56) References Cited

U.S. PATENT DOCUMENTS 6,247,356 B1 *  6/2001  Merck, Jr. ................ G01N 3/42
                                                            73/82
8,950,260 B2 *  2/2015  Gelinske ................. G01F 1/666
                                                            73/1.16

(Continued)

FOREIGN PATENT DOCUMENTS

CN            103412054 A  *  11/2013   ............. G01N 29/26

*Primary Examiner* — Manish S Shah
*Assistant Examiner* — Suman K Nath
(74) *Attorney, Agent, or Firm* — Matthias Scholl, PC; Matthias Scholl (57) ABSTRACT

An adjustable fixing device for acoustic emission test sensors for rock damage testing, the device including: a fixing frame; installation bases operating to accommodate the acoustic emission test sensors, respectively; fixing assemblies operating to fix the acoustic emission test sensors in the installation bases; and installation mechanisms operating to install the installation bases on the fixing frame. The fixing frame is a rectangular frame, and at least a pair of opposite frame walls of four frame walls is provided with installation slots adapted to install the installation mechanisms. The installation slots positioned at different frame walls are in a same cross section of the rectangular frame. Each of the installation bases is a cylinder structure. The cylinder structure includes: a cavity corresponding to an outer edge of each of the acoustic emission test sensors, and a wall including a gap for leading out wires of each sensor.

6 Claims, 11 Drawing Sheets

(58) Field of Classification Search
USPC .......................... 73/587, 622, 623, 865, 432
See application file for complete search history.

(56) References Cited

U.S. PATENT DOCUMENTS

| | | | |
|---|---|---|---|
| 2010/0313661 A1* | 12/2010 | Liu | ................ G01N 29/14 73/587 |
| 2010/0313662 A1* | 12/2010 | Liu | ................ G01N 29/14 73/587 |
| 2012/0261363 A1* | 10/2012 | Liu | ................ G01N 29/14 211/26 |

* cited by examiner

ADJUSTABLE FIXING DEVICE FOR ACOUSTIC EMISSION TEST SENSORS FOR ROCK DAMAGE TESTING

CROSS-REFERENCE TO RELATED APPLICATIONS

Pursuant to 35 U.S.C. § 119 and the Paris Convention Treaty, this application claims the benefit of Chinese Patent Application No. 201510066706.2 filed Feb. 9, 2015, the contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a fixing device for acoustic emission test sensors for damage testing of material samples.

Description of the Related Art

Conventionally, acoustic emission test sensors are fixed by adhesive tape or rubber band. However, adhesive tape tends to increase the pressure on the sensors and even damage them, and rubber band cannot guarantee good contact between the acoustic emission test sensors and samples. For these reasons, conventional fixing methods have the following shortcomings: (1) the fixing methods cannot ensure accurate positioning of the sensors; (2) the fixing methods produce signal noise and artifacts, which increases the difficulty in analyzing the test results; and (3) the fixing methods are of limited use with deformation test sensors.

SUMMARY OF THE INVENTION

In view of the above-described problems, it is one objective of the invention to provide an adjustable fixing device for acoustic emission test sensors for rock damage testing to ensure that centers of end surfaces of the oppositely arranged sensors are opposite to each other and are consistent with the positions set by control software so as to improve efficiency, accuracy, and authenticity of the test.

To achieve the above objective, in accordance with one embodiment of the invention, there is provided an adjustable fixing device for acoustic emission test sensors for rock damage testing. The device comprises: a fixing frame; installation bases, the installation bases operating to accommodate the acoustic emission test sensors, respectively; fixing assemblies, the fixing assemblies operating to fix the acoustic emission test sensors in the installation bases; and installation mechanisms, the installation mechanisms operating to install the installation bases on the fixing frame. The fixing frame is a rectangular frame, and at least a pair of opposite frame walls of four frame walls is provided with installation slots adapted to install the installation mechanisms. The installation slots positioned at different frame walls are in a same cross section of the rectangular frame. Each of the installation bases is a cylinder structure, and the cylinder structure comprises: a cavity corresponding to an outer edge of each of the acoustic emission test sensors, and a wall comprising a gap for leading out wires of each sensor. The installation mechanisms are adapted to automatically and axially adjust positions of the installation bases. The installation mechanisms are at least two in number. The installation mechanisms are installed on the rectangular frame via the installation slots, and every two installation mechanisms are oppositely disposed to enable sensors fixed therein are opposite to each other and lines perpendicular to the centers of the end surfaces of the opposite arranged sensors coincide with each other.

In a class of this embodiment, the fixing frame is an integrated rectangular frame or an assembled rectangular frame.

In a class of this embodiment, preferably, a scale is arranged above or below each of the installation slots for marking installation positions of the installation mechanisms so that the installation position is clear, which brings convenience.

In a class of this embodiment, each of the fixing assemblies comprises: a split ring spring for binding each acoustic emission test sensor in each installation base, and a locking structure for locking the split ring spring. The locking structure is a clasp locking structure, or a bolt-nut locking structure, or other locking structures.

In a class of this embodiment, the gap disposed on the wall of the cylinder structure of each of the installation bases is used for leading out the wires of the sensors. In the structure that adopts the split ring spring to fix the acoustic emission test sensor in the installation base, the gap of the cylinder structure is also a constituent part of the fixing assembly. The gap should not be too large and an angle of the gap is usually is less than or equal to 120°.

In a class of this embodiment, each of the installation mechanisms comprises: a sliding bar in fixed connection with each installation base; a spring which is sleeved on the sliding bar and has one end acting on each installation base and the other end acting on an inner wall of the fixing frame; and a support base adapted to install the sliding bar. The support base adopts a structure of a guide tube, and an outer diameter of the guide tube matches a width of each of the installation slots. An outer wall of the guide tube is provided with threads, and the guide tube is fixed in the installation slot via a thread pair formed by nuts disposed on the inner wall and an outer wall of the fixing frame. An inner diameter of the guide tube matches an outer diameter of the sliding bar to form a sliding pair. The sliding bar is axially slidably disposed in the guide tube serving as the support base. A position-limit structure is disposed on a part of the sliding bar protruding from the guide tube for limiting axial sliding of the sliding bar.

In a class of this embodiment, the position-limit structure for limiting the axial sliding of the sliding bar is formed by threads arranged on the sliding bar and a mating nut, or by a pin hole arranged on the sliding bar and a mating pin. The sliding bar can be fixed on and connected with the installation base by welding or a thread pair.

In a class of this embodiment, an external of the guide tube serving as the support base is provided with a mark configured to point at the scale arranged above or below each of the installation slots, so that the installation position is clear.

In a class of this embodiment, the fixing frame is provided with a slot for leading out the wires of the acoustic emission test sensor.

Advantages of the adjustable fixing device for the acoustic emission test sensors for the rock damage testing according to embodiments of the invention are summarized as follows:

The four installation mechanisms which can automatically and axially adjust positions of the installation bases are pairwise arranged on the fixing frame on the same section plane in two directions which are perpendicular to each other. The installation mechanism ensures that the acoustic emission test sensor disposed in the installation base always contacts the centers of the end faces of the sensor and that the installation positions of the sensors are consistent with the positions set by the control program. That is, the centers of the end faces of the four pairwise and symmetrically installed acoustic emission test sensors just pass through the given testing direction. Thus, not only is the test information acquired from the test of the same test piece as much as possible, but also the position of the centers of the end faces of the sensors are consistent with the positions set in the control program during the installation and the test of the test piece, thus ensuring efficiency, accuracy and authenticity of the test. The fixing device of the invention ensures that the installation positions of the sensors are consistent with the positions set by the program and that the sensors are always disposed at the preset positions during the process of smearing coupling agent and the centers of the end faces of the sensors and the test piece are in a good coupling state.

The installation mechanisms of the invention are adapted to automatically and axially adjust positions of the installation bases. The springs are sleeved on the sliding bars between the installation bases and the inner wall of fixing frame, so that the end face of the sensors tightly contact the surface of the test piece, the stresses imposed on the acoustic emission test sensors are not increased during the radial swelling of the test piece in the test, and the sensors are under consistent stress in the test of the same batch of test pieces. The invention can not only reduce pseudo signals' influence on test results but also extend the service life of the acoustic emission test sensor. As for the fixing device disclosed in the prior art, since two parallel cantilever rods for fixing two acoustic emission test sensors are connected with each other by a connecting rod, the connecting rod is arranged on one side of the connecting rod when two acoustic emission test sensors are arranged on the test piece; and when the test piece is damaged abruptly in the test, the whole structure formed by the fixing device and the two acoustic emission test sensors swing towards the side where the connecting rod is disposed and then the side may run into the loading frame of the testing machine to damage the sensors and reduce test accuracy. Since the fixing device of the invention has an integrated structure and is nested outside the test piece, the fixing device suspends in the air when the test piece is damaged abruptly, thus preventing the fixing device from running into the testing machine and protecting the sensors more effectively.

During the whole test from loading of the test piece to the damage of the test piece, the shape of the test piece changes all the time. In the fixing device in the prior art, a connection length of a connection rod adapted to fixedly connect to a cantilever arm is fixed, two arm rods for arranging sensors change from the initial parallel state into a splay state, which lowers effectiveness of the coupling of the sensor transverse plane center and the test piece center and influences test accuracy. The sensors of the invention are arranged on the fixing frame by installation bases and installation mechanisms. During the process of test piece deformation, the sliding bars which are fixed on and connected with the sensors can stretch out and draw back freely in the guide tubes which serve as installation bases. Due to the springs sleeved on the sliding bars, the test sensors and the test pieces are always in the best coupling state. The invention overcomes the shortcomings of fixing devices in the prior art. The fixing device of the invention also has the advantages of the prior art (excluding universal arbitrary adjustment).

Because the installation mechanism is installed in the installation slot of the frame wall, and the installation position is transversely adjustable, the use of the adjustable fixing device of the invention ensures that the centers of end surfaces of the oppositely arranged sensors are adjustable in accordance with the shape of the test pieces, and that the number of the sensors is also adjustable, overcoming the difficulty of nonadjustable fixing device when using test pieces which have irregular cross sections and need two pairs or more sensors to conduct test in the prior art.

BRIEF DESCRIPTION OF THE DRAWINGS

The invention is described hereinbelow with reference to the accompanying drawings, in which:

FIG. 9-1 is a partial top view of a first assembled structure of an assembled frame in FIG. 8;

FIG. 9-2 is a rear view of FIG. 9-1;

FIG. 9-3 is a rear view illustrating a connection in FIG. 9-1;

FIG. 10-1 is a partial top view of a second assembled structure of an assembled frame in FIG. 8;

FIG. 10-2 is a rear view of FIG. 10-1;

FIG. 10-3 is a rear view illustrating a connection in FIG. 10-1;

FIG. 11-1 is a top section view of an adjustable fixing device for acoustic emission test sensors for rock damage testing in Example 3; the fixing frame is an integrated frame, and a cross section of a test piece is a large-size cylinder; two parallel fixing devices are adapted to fix a test piece platform;

FIG. 11-2 is a side view of FIG. 11-1; and

FIG. 11-3 is a front view of FIG. 11-1.

In the drawings, the following reference numbers are used: 1. Fixing frame; 2. Support base; 3. Sliding bar; 4. Position-limit nut; 5. Spring; 6. Installation base; 7. Split ring spring; 8. Clasp; 9. Wire of sensor; 10. Slot for leading out wire of sensor; 11. Acoustic emission test sensor; 12. Test piece; 13. Lock bolt; 14. Installation slot; 15. Limit spigot; 16. First frame member; 17. Positioning pin; 18. Second frame member; 20. First limit nut; 21. Second limit nut; 61. Cavity; and 62. Wall.

DETAILED DESCRIPTION OF THE EMBODIMENTS

For further illustrating the invention, experiments detailing an adjustable fixing device for acoustic emission test sensors for rock damage testing are described below. It should be noted that the following examples are intended to describe and not to limit the invention.

EXAMPLE 1

An adjustable fixing device for acoustic emission test sensors for rock damage testing is provided in this example, as shown in FIGS. 1, 2, 3, 5, and 6. The fixing device is adapted to test an irregular rectangular face rock sample as a test piece. The fixing device comprises: a fixing frame 1, an installation bases 6 operating to accommodate acoustic emission test sensors 11, fixing assemblies operating to fix the acoustic emission test sensors 11 in the installation bases 6, and installation mechanisms operating to install the installation bases 6 on the fixing frame 1. The fixing frame 1 is a rectangular frame, and four frame walls are provided with installation slots 14 adapted to install the installation mechanisms, respectively. The installation slots positioned at different frame walls are in a same cross section. Each of the installation bases is a cylinder with a closed end, and a cavity 61 of the cylinder matches an outer edge of the acoustic emission test sensor 11. A gap for leading out wires of the sensor is disposed on the wall 62 of the installation base, and an angle of the gap is 80°. Each of the fixing assemblies configured to fix the acoustic emission test sensor 11 in the installation base 6 is formed by a split ring spring 7 which binds the acoustic emission test sensor 11 in the installation base and a locking structure which locks the split ring spring. The locking structure is a clasp 8 locking device. Each installation mechanism is adapted to automatically and axially adjust positions of the installation bases and comprises: a sliding bar 3 in fixed connection with the installation base 6; a spring 5 which is sleeved on the sliding bar 3 and has one end acting on the installation base and the other end acting on an inner wall of the fixing frame 1; and a support base 2 adapted to install the sliding bar. The support base 2 adopts a structure of a guide tube. An outer diameter of the guide tube matches a width of each of the installation slots. An outer wall of the guide tube is provided with threads, thus the guide tube is fixed in the installation slot via a thread pair formed by a first limit nut 20 on the outer wall of the fixing frame wall and a second limit nut 21 on an inner wall of the fixing frame wall. An inner diameter of the guide tube matches an outer diameter of the sliding bar 3 to form a sliding pair. The sliding bar 3 travels through an installation hole on the fixing frame 1 and is axially slidably disposed in the guide tube serving as the support base 2. A position-limit structure is disposed on a part of the sliding bar 3 protruding from the support base 2 for limiting axial sliding of the sliding bar. The position-limit structure is formed by threads arranged on the sliding bar 3 and a position—limit nut 4 matching the threads and is adapted to limit the axial sliding of the sliding bar 3. The installation mechanisms are six in number. The opposite frame walls in the direction of the side view are provided with two pairs of oppositely disposed installation mechanism, in which one pair acts on the large cross section of the test piece and another pair acts on the small cross section of the test piece. The opposite frame walls in the direction of the front view are provided with one pair of oppositely disposed installation mechanisms.

A method for using the adjustable fixing device for acoustic emission test sensors for rock damage testing of the invention is as follows:

1. According to the size of the rock sample and the possible deformation of the rock sample is damaged, the suitable length of springs 5 is chosen. Six acoustic emission test sensors 11 are respectively fixed and arranged in the cylinders serving as the installation bases in the fixing device. The position-limit nuts arranged on the sliding bars of the installation mechanisms are adjusted to make the springs 5 which are sleeved on the sliding bars 3 of the installation mechanisms always remain in compression states during the whole test process so as to ensure that the centers of the end faces of the acoustic emission test sensors effectively contact the surface of the rock sample. It is to be noted that the amount of compression of the springs on the sliding bars should be the same when position-limit nuts are adjusted. In addition, when the acoustic emission test sensors are arranged on the test piece after the position-limit nuts are adjusted, the position-limit nuts should be arranged between free ends of the sliding screw 3 and free ends of the guide tubes which serve as the installation base 2, and cannot contact the free ends of the guide tubes. Thus, the two pairwise arranged acoustic emission test sensors 11 can move towards opposite directions when the size of the rock sample reduces horizontally, during the rock deformation process; and the two pairwise arranged acoustic emission test sensors 11 compress the springs and move towards opposite directions due to rock deformation when the size of the rock sample enlarges.

2. After the distances and the nut positions are adjusted, the wires of the acoustic emission test sensors 11 are respectively fixed in the slots 10 for leading out the wire.

3. According to the test, other test sensors are installed, and then the acoustic emission test sensors are fixed on the test piece in the vicinity of the end thereof.

4. The test piece installed with the acoustic emission test sensors are arranged on the testing machine for test.

After the above installation process, when the test piece expands horizontally in the test, the distance between the end faces of every two opposite disposed test sensors can be slightly changed by the springs. And the test sensors are attached to the surface of the test piece and the end faces of every two opposite disposed test sensors always keep in parallel with each other so as to ensure the accuracy and the authenticity of test signals.

EXAMPLE 2

Figure 1:
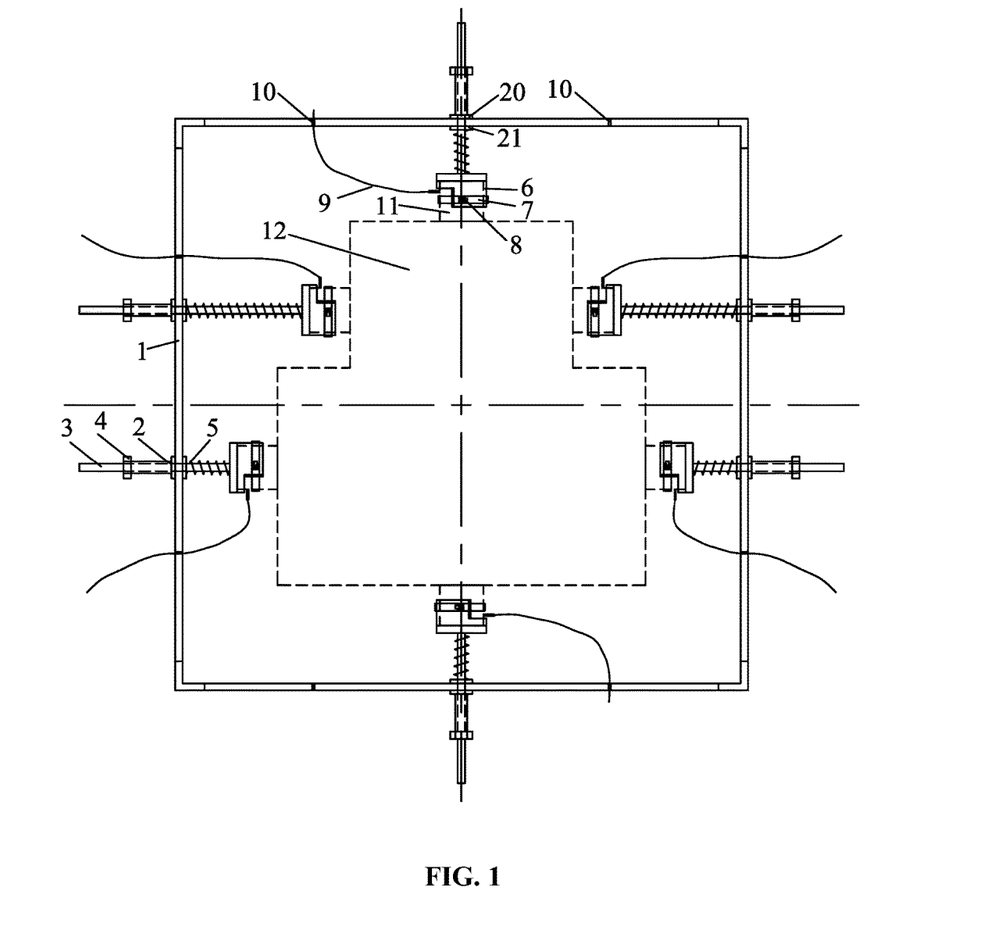
FIG. 1 is a top view of an adjustable fixing device for acoustic emission test sensors for rock damage testing in Example 1; the fixing frame is an integrated frame, and a cross section of a test piece is an irregular rectangular face.
Figure 2:
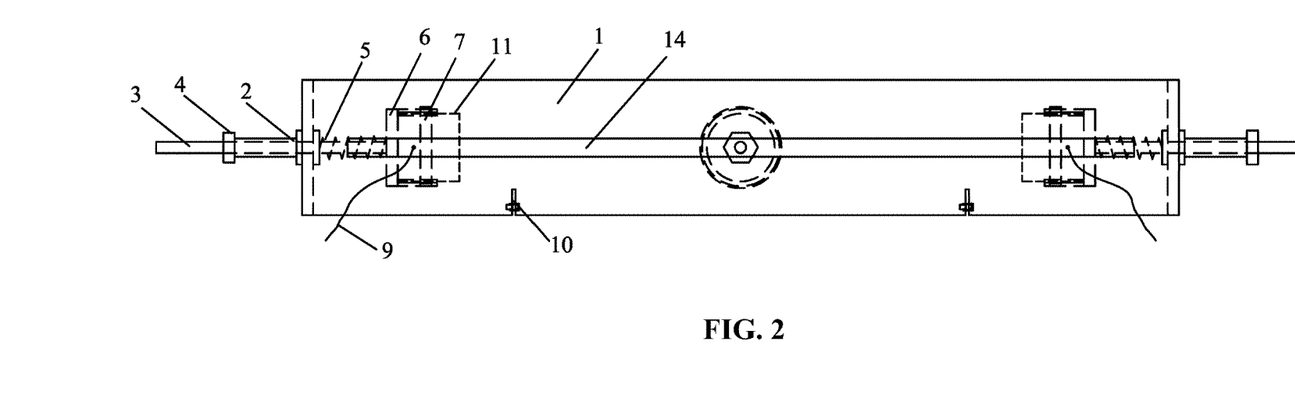
FIG. 2 is a front view of FIG. 1.
Figure 3:
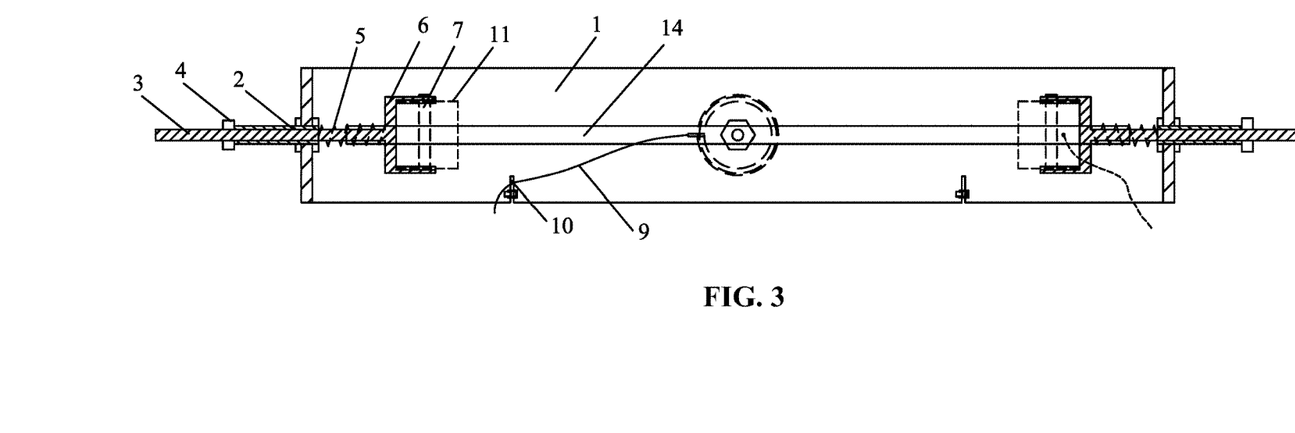
FIG. 3 is a front section view of the fixing device shown in the FIG. 1.
Figure 4:
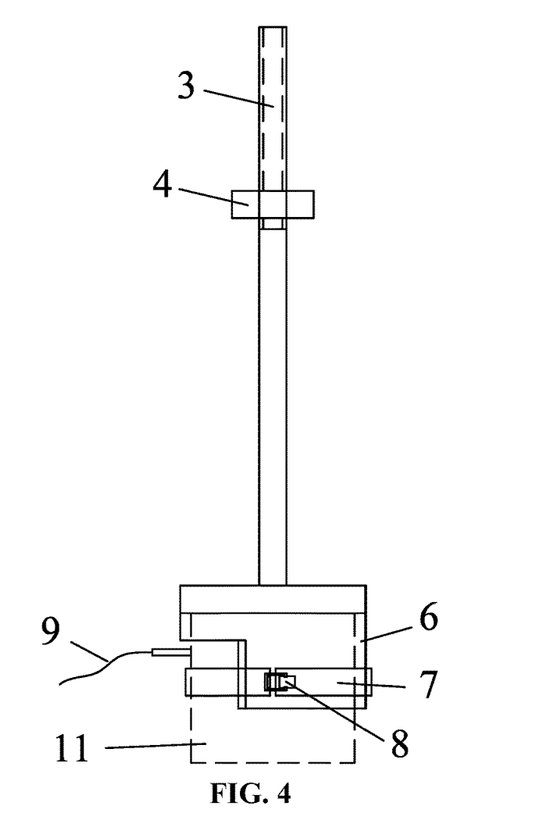
FIG. 4 is a structure diagram illustrating connection between an installation base and a sliding bar.
Figure 5:
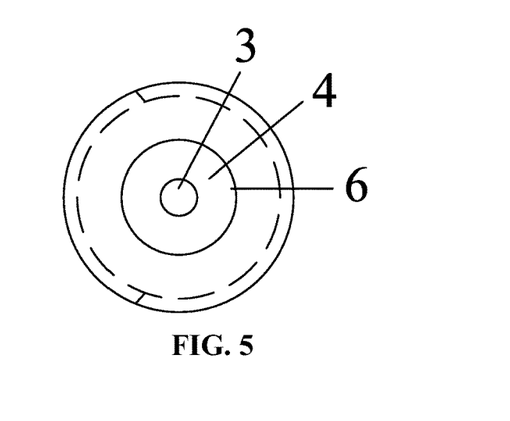
FIG. 5 is a top view of FIG. 4.
Figure 6:
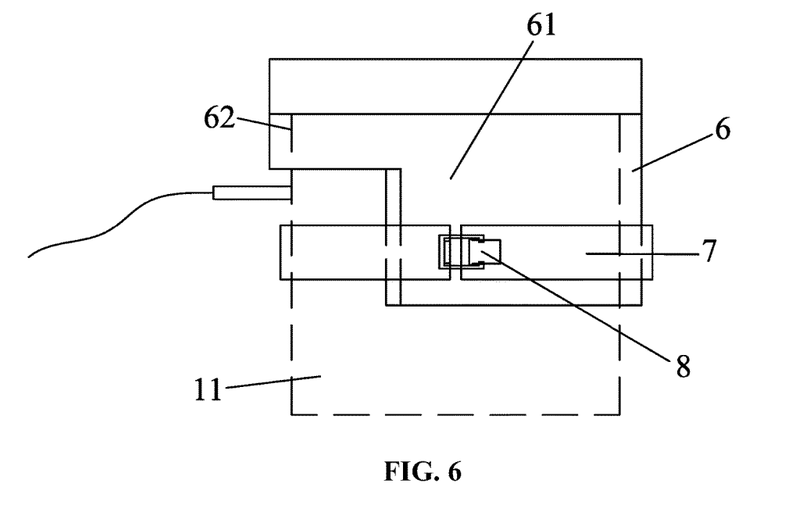
FIG. 6 is a structure diagram of a first mode for fixing a sensor in an installation base.
Figure 7:
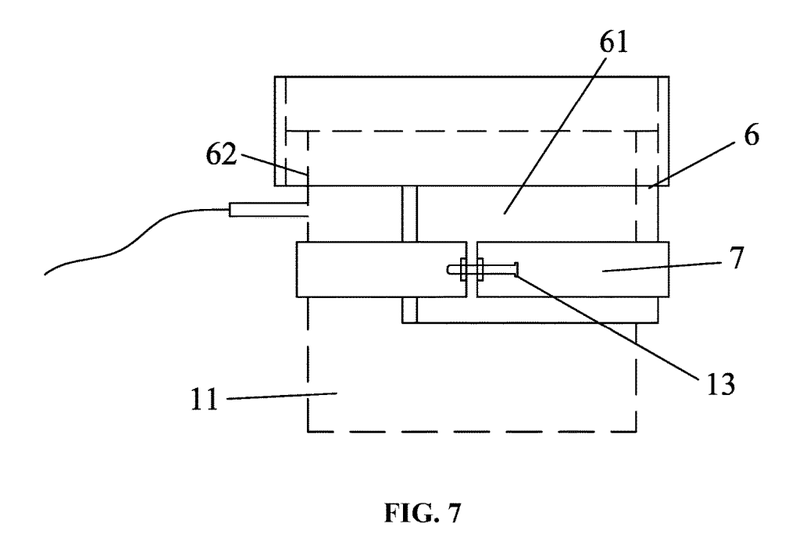
FIG. 7 is a structure diagram of a second mode for fixing a sensor in an installation base.
Figure 8:
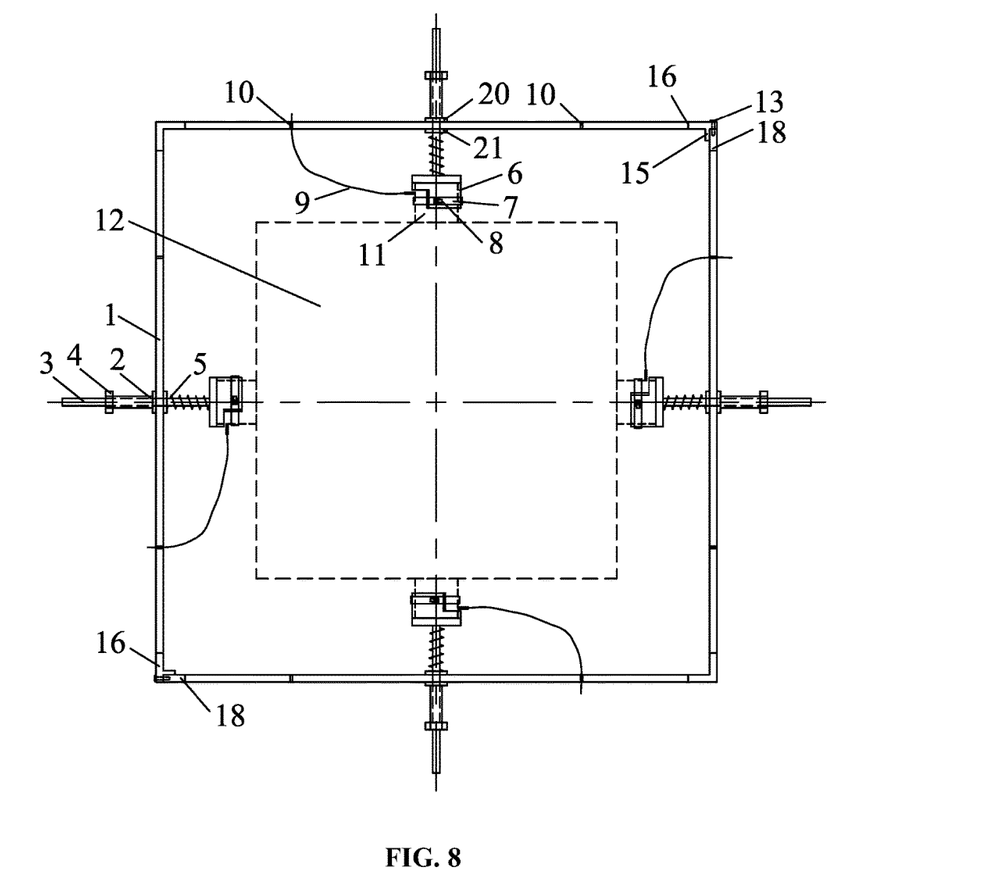
FIG. 8 is a top view of an adjustable fixing device for acoustic emission test sensors for rock damage testing in Example 2; the fixing frame is an assembled frame, and a cross section of a test piece is a regular rectangular face.
Figure 91:
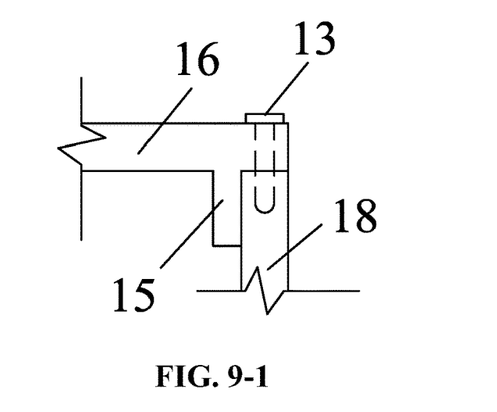
Figure 92:
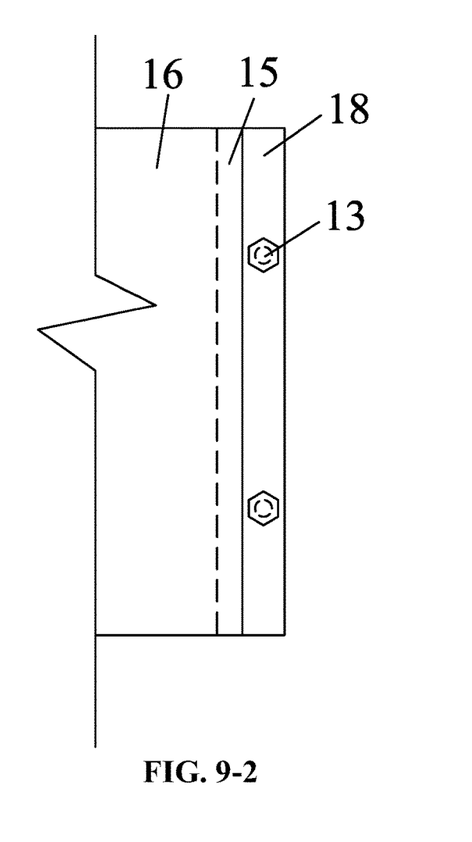
Figure 93:
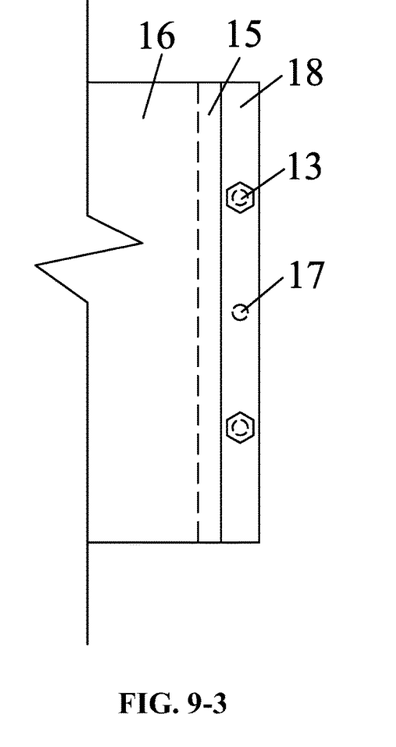
Figure 101:
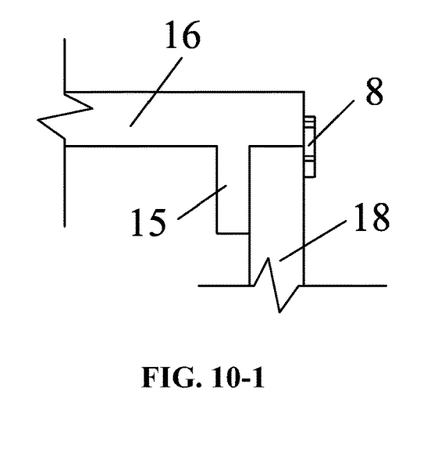
Figure 102:
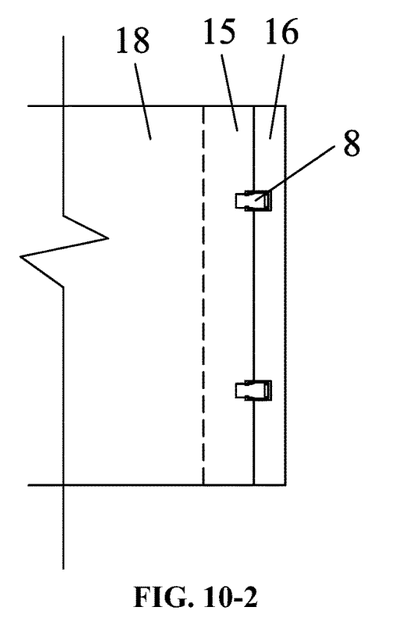
Figure 103:
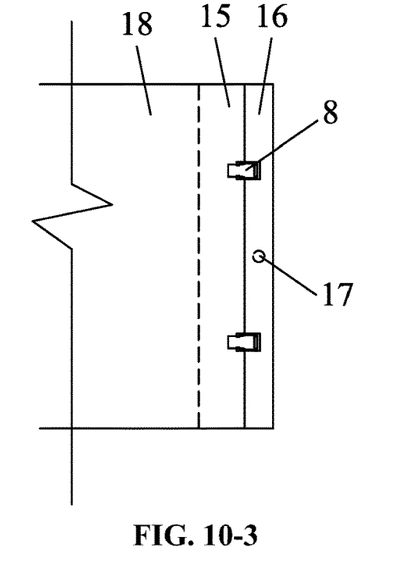

A structure of an adjustable fixing device for acoustic emission test sensors for rock damage testing is shown in FIGS. 8, 9-1, and 9-3, and the test piece is a rectangular rock sample. The structure of the fixing device in this example is the same as that of Example 1 except that: (1) the fixing frame 1 is an assembled rectangular loop-shaped fixing frame 1 assembled by a first frame member 16 and a second frame member 18 via fixing structures; the structures are shown in FIGS. 9-1 and 9-3, including a limit spigot 15 disposed on an end of a first frame member 16, a positioning pin 17, and a lock bolt 13. The first frame member 16 and the second frame member 18 are integrated to be a rectangular loop-shaped frame via the positioning pin 17 and a lock bolt 13; and (2) each of the installation slots of the four frame walls is provided with one installation mechanism, and every two installation mechanisms are oppositely arranged.

EXAMPLE 3

Figure 111:
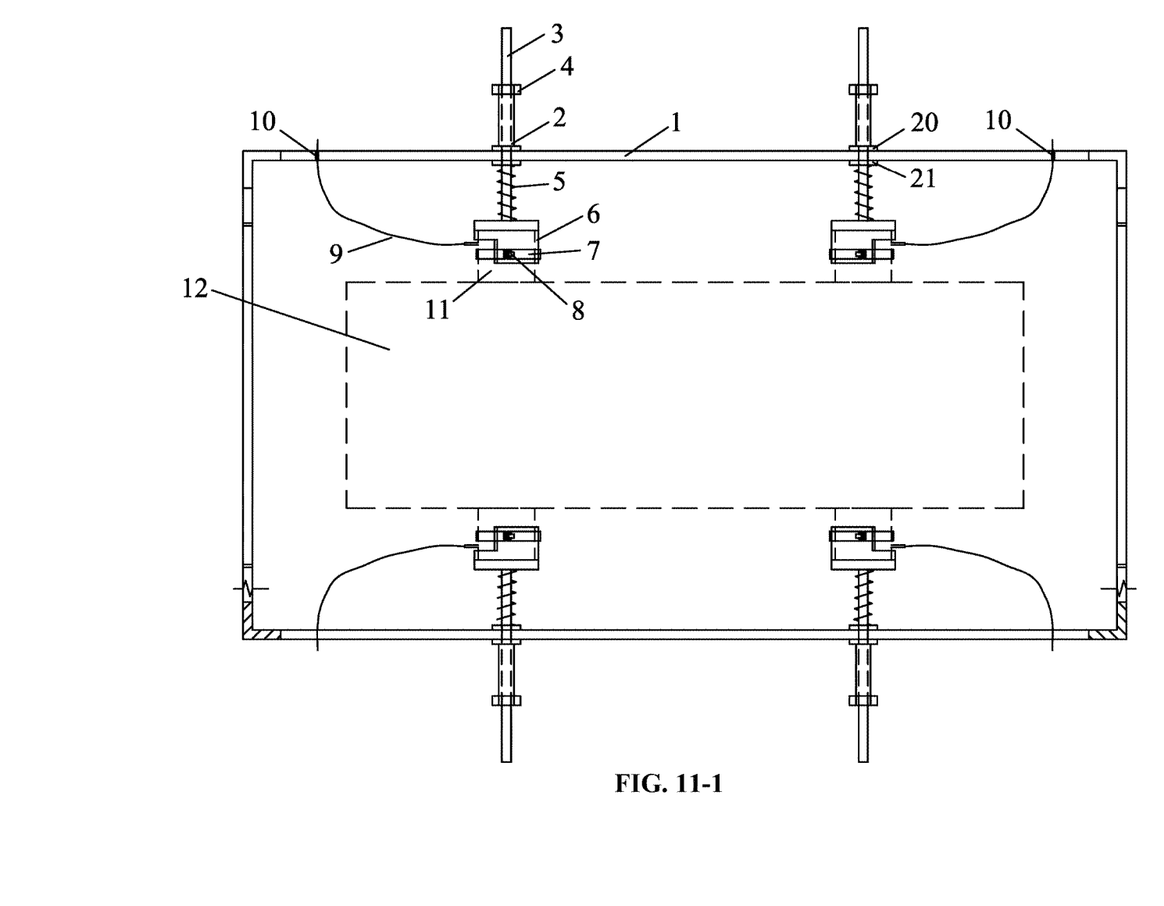
Figure 112:
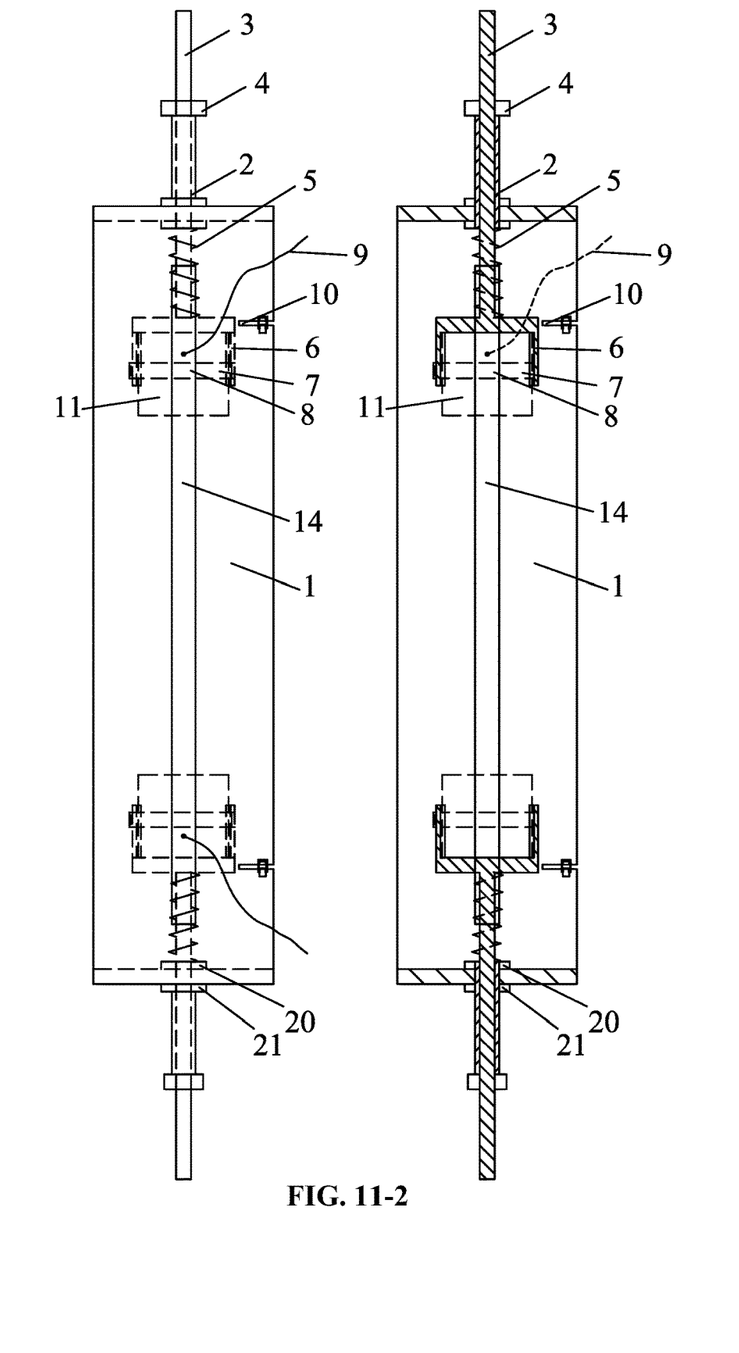
Figure 113:
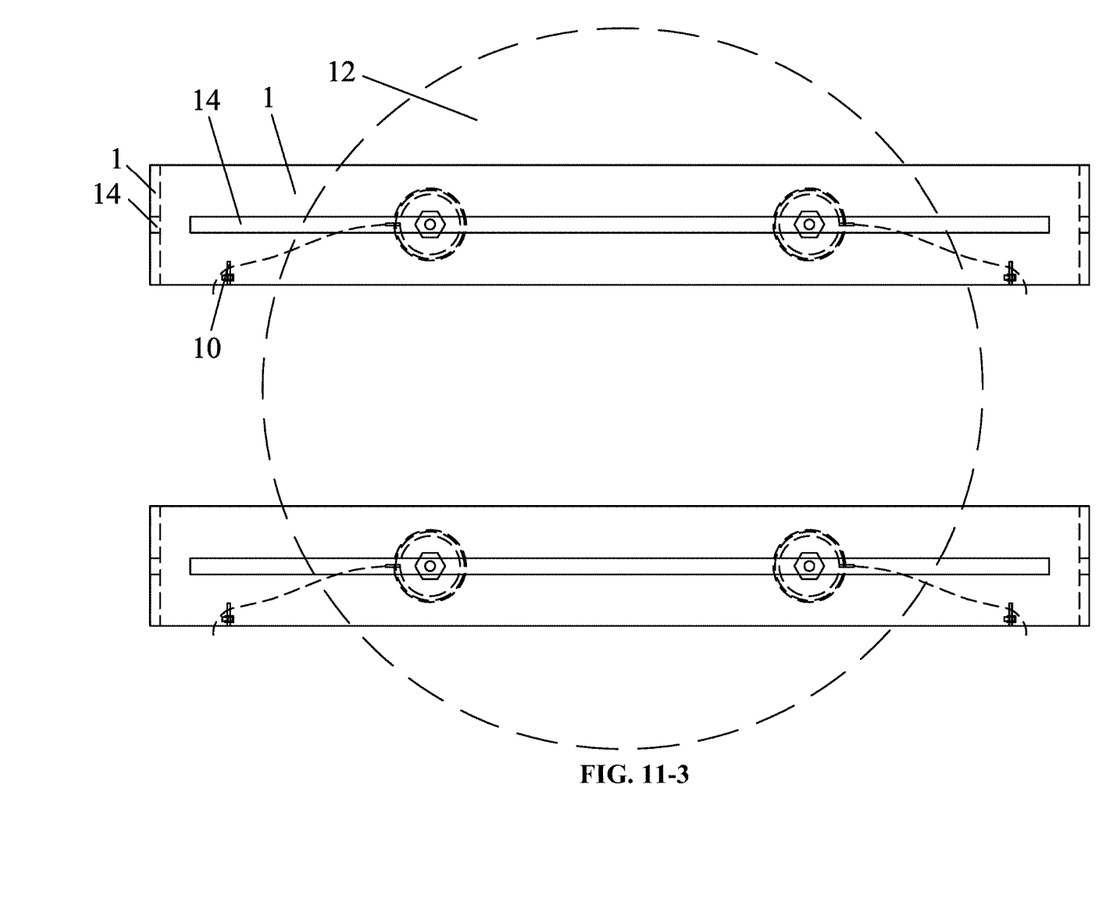

As shown in FIGS. 12-1, 12-2, and 12-3, the fixing frame is an integrated frame, and a cross section of a test piece is a large-size cylinder; two fixing devices are arranged in parallel to fix plane surfaces of the test pieces. The fixing frame of each fixing device is the integrated fixing frame. The structure of the fixing device in this example is the same as that of Example 1 except that: only installation slots of the opposite frame walls in the direction of the front view are provided with two pairs of oppositely disposed installation mechanisms, and the installation slots of opposite frame walls in the direction of the side view are not provided with installation mechanisms.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An adjustable fixing device for fixing acoustic emission test sensors for rock damage testing, the device comprising:
   a) a fixing frame;
   b) installation bases, the installation bases operating to accommodate the acoustic emission test sensors, respectively;
   c) fixing assemblies, the fixing assemblies operating to fix the acoustic emission test sensors in the installation bases; and
   d) installation mechanisms, the installation mechanisms operating to install the installation bases on the fixing frame;
   wherein:
   the fixing frame is a rectangular frame, and at least a pair of opposite frame walls of four frame walls is provided with installation slots adapted to install the installation mechanisms; the installation slots positioned at different frame walls are in a same cross section of the rectangular frame;
   each of the installation bases is a cylinder structure; the cylinder structure comprises: a cavity corresponding to an outer edge of each of the acoustic emission test sensors, and a wall comprising a gap for leading out wires of each sensor;
   the installation mechanisms are adapted to automatically and axially adjust positions of the installation bases; the installation mechanisms are at least two in number; the installation mechanisms are installed on the rectangular frame via the installation slots, and every two installation mechanisms are oppositely disposed to enable sensors fixed therein are opposite to each other and lines perpendicular to the centers of the end surfaces of the opposite arranged sensors coincide with each other;
   each of the installation mechanisms comprises: a sliding bar in fixed connection with each installation base; a spring which is sleeved on the sliding bar and has one end acting on each installation base and the other end acting on an inner wall of the fixing frame; and a support base adapted to install the sliding bar;
   the support base adopts a structure of a guide tube, and an outer diameter of the guide tube matches a width of each of the installation slots; an outer wall of the guide tube is provided with threads, and the guide tube is fixed in the installation slot via a thread pair formed by nuts disposed on the inner wall and an outer wall of the fixing frame; and
   an inner diameter of the guide tube matches an outer diameter of the sliding bar to form a sliding pair; the sliding bar is axially slidably disposed in the guide tube serving as the support base; a position-limit structure is disposed on a part of the sliding bar protruding from the guide tube for limiting axial sliding of the sliding bar.

2. The device of claim 1, wherein the position-limit structure for limiting the axial sliding of the sliding bar is formed by threads arranged on the sliding bar and a mating nut, or by a pin hole arranged on the sliding bar and a mating pin.

3. The device of claim 2, wherein the fixing frame is an integrated rectangular frame or an assembled rectangular frame.

4. The device of claim 2, wherein an angle of the gap of the cylinder structure of each of the installation bases is less than or equal to 120°.

5. The device of claim 2, wherein each of the fixing assemblies comprises:
   a split ring spring for binding each acoustic emission test sensor in each installation base, and a locking structure for locking the split ring spring.

6. The device of claim 4, wherein the locking structure is a clasp locking structure, or a bolt-nut locking structure.

* * * * *